United States Patent
Morris et al.

(10) Patent No.: US 7,025,456 B2
(45) Date of Patent: Apr. 11, 2006

(54) DIFFRACTIVE LENSES FOR VISION CORRECTION

(75) Inventors: G. Michael Morris, Victor, NY (US); Dale A. Buralli, Rochester, NY (US); Richard J. Federico, Spencerport, NY (US)

(73) Assignee: Apollo Optical Systems, LLC, Rochester, NY (US)

( * ) Notice: Subject to any disclaimer, the term of this patent is extended or adjusted under 35 U.S.C. 154(b) by 0 days.

(21) Appl. No.: 10/922,600

(22) Filed: Aug. 20, 2004

(65) Prior Publication Data

US 2006/0050234 A1    Mar. 9, 2006

(51) Int. Cl.
G02C 7/06 (2006.01)
(52) U.S. Cl. .......................... 351/168; 351/161; 623/6.3
(58) Field of Classification Search ................ 351/161, 351/168; 623/6.3, 6.31
See application file for complete search history.

(56) References Cited

U.S. PATENT DOCUMENTS

| | | | |
|---|---|---|---|
| 3,004,470 A | 10/1961 | Ruhle | |
| 4,162,122 A | 7/1979 | Cohen | |
| 4,210,391 A | 7/1980 | Cohen | |
| 4,338,005 A | 7/1982 | Cohen | |
| 4,340,283 A | 7/1982 | Cohen | |
| 4,541,697 A | 9/1985 | Remijan | |
| 4,637,697 A | 1/1987 | Freeman | |
| 4,641,934 A | 2/1987 | Freeman | |
| 4,642,112 A | 2/1987 | Freeman | |
| 4,655,565 A | 4/1987 | Freeman | |
| 4,769,033 A | 9/1988 | Nordan | |
| 4,830,481 A | 5/1989 | Futhey et al. | |
| 4,881,804 A | 11/1989 | Cohen | |
| 4,881,805 A | 11/1989 | Cohen | |
| 4,936,665 A | 6/1990 | Whitney | |
| 4,936,666 A | 6/1990 | Futhey | |
| 4,995,714 A | 2/1991 | Cohen | |
| 4,995,715 A | 2/1991 | Cohen | |
| 5,013,133 A | 5/1991 | Buralli et al. | |
| 5,016,977 A | 5/1991 | Baude et al. | |
| 5,017,000 A | 5/1991 | Cohen | |
| 5,054,905 A | 10/1991 | Cohen | |
| 5,056,908 A | 10/1991 | Cohen | |
| 5,071,207 A | 12/1991 | Ceglio et al. | |
| 5,076,684 A | 12/1991 | Simpson et al. | |
| 5,096,285 A | 3/1992 | Silberman | |

(Continued)

OTHER PUBLICATIONS

Nordan, L., The Vision Membrane, Cataract & Refractive Surgery Today (2003).

(Continued)

*Primary Examiner*—Jordan M. Schwartz
(74) *Attorney, Agent, or Firm*—Kenneth J. Lukacher

(57) ABSTRACT

Diffractive lenses for vision correction are provided on a lens body having a first diffractive structure for splitting light into two or more diffractive orders to different focal distances or ranges, and a second diffractive structure, referred to as a multiorder diffractive (MOD) structure, for diffracting light at different wavelengths into a plurality of different diffractive orders to a common focal distance or range. In a bifocal application, the first and second diffractive structures in combination define the base power for distance vision correction and add power for near vision correction of the lens. The first and second diffractive structures may be combined on the same surface or located on different surfaces of the lens. An optical element, such as a substrate or coating, may be integrated along one or both surfaces of the lens to provide the lens with smooth outer surface(s).

38 Claims, 14 Drawing Sheets

U.S. PATENT DOCUMENTS

| | | |
|---|---|---|
| 5,100,226 A | 3/1992 | Freeman |
| 5,104,212 A | 4/1992 | Taboury et al. |
| 5,114,220 A | 5/1992 | Baude et al. |
| 5,116,111 A | 5/1992 | Simpson et al. |
| 5,117,306 A | 5/1992 | Cohen |
| 5,120,120 A | 6/1992 | Cohen |
| 5,121,979 A | 6/1992 | Cohen |
| 5,121,980 A | 6/1992 | Cohen |
| 5,129,718 A | 7/1992 | Futhey et al. |
| 5,144,483 A | 9/1992 | Cohen |
| 5,152,788 A | 10/1992 | Isaacson et al. |
| 5,153,778 A | 10/1992 | Sasian-Alvarado |
| 5,178,636 A | 1/1993 | Silberman |
| 5,198,844 A | 3/1993 | Roffman et al. |
| 5,229,797 A | 7/1993 | Futhey et al. |
| 5,237,451 A | 8/1993 | Saxe |
| 5,257,132 A | 10/1993 | Ceglio et al. |
| 5,281,294 A | 1/1994 | Freeman et al. |
| 5,285,314 A | 2/1994 | Futhey |
| 5,296,881 A | 3/1994 | Freeman |
| 5,344,447 A | 9/1994 | Swanson |
| 5,349,396 A | 9/1994 | Roffman et al. |
| 5,384,606 A | 1/1995 | Koch et al. |
| 5,408,281 A | 4/1995 | Zhang |
| 5,442,480 A | 8/1995 | Swanson et al. |
| 5,448,312 A | 9/1995 | Roffman et al. |
| 5,485,228 A | 1/1996 | Roffman et al. |
| 5,507,806 A | 4/1996 | Blake |
| 5,507,979 A | 4/1996 | Roffman et al. |
| 5,512,220 A | 4/1996 | Roffman et al. |
| 5,517,260 A | 5/1996 | Glady et al. |
| 5,574,518 A | 11/1996 | Mercure |
| 5,589,982 A | 12/1996 | Faklis et al. |
| 5,682,223 A | 10/1997 | Menezes et al. |
| 5,684,560 A | 11/1997 | Roffman et al. |
| 5,699,142 A | 12/1997 | Lee et al. |
| 5,715,031 A | 2/1998 | Roffman et al. |
| 5,724,120 A | 3/1998 | Svochak et al. |
| 5,724,258 A | 3/1998 | Roffman |
| 5,748,282 A | 5/1998 | Freeman |
| 5,760,871 A | 6/1998 | Kosoburd et al. |
| 5,798,817 A | 8/1998 | De Carle |
| 5,800,532 A | 9/1998 | Lieberman |
| 5,805,260 A | 9/1998 | Roffman et al. |
| 5,847,802 A | 12/1998 | Menezes et al. |
| 5,895,422 A | 4/1999 | Hauber |
| 5,929,969 A | 7/1999 | Roffman |
| 6,120,148 A | 9/2000 | Fiala et al. |
| 6,176,878 B1 | 1/2001 | Gwon et al. |
| 6,179,420 B1 | 1/2001 | Roffman et al. |
| 6,231,603 B1 | 5/2001 | Lang et al. |
| 6,250,757 B1 | 6/2001 | Roffman et al. |
| 6,270,220 B1 | 8/2001 | Keren |
| 6,325,510 B1 | 12/2001 | Golub et al. |
| 6,330,110 B1 | 12/2001 | Nakai |
| 6,364,483 B1 | 4/2002 | Grossinger et al. |
| 6,406,494 B1 | 6/2002 | Laguette et al. |
| 6,457,826 B1 | 10/2002 | Lett |
| 6,474,814 B1 | 11/2002 | Griffin |
| 6,511,178 B1 | 1/2003 | Roffman et al. |
| 6,951,391 B1 * | 10/2005 | Morris et al. ............... 351/168 |
| 2001/0018612 A1 | 8/2001 | Carson et al. |
| 2002/0016630 A1 | 2/2002 | Lang |
| 2002/0120329 A1 | 8/2002 | Lang et al. |
| 2002/0143394 A1 | 10/2002 | Lang |
| 2002/0161435 A1 | 10/2002 | Portney |
| 2002/0193876 A1 | 12/2002 | Lang et al. |
| 2003/0014107 A1 | 1/2003 | Reynard |
| 2003/0018385 A1 | 1/2003 | Tran et al. |
| 2003/0035214 A1 | 2/2003 | Pandya |
| 2003/0045931 A1 | 3/2003 | Lang |
| 2003/0097176 A1 | 5/2003 | Nordan et al. |
| 2003/0220687 A1 * | 11/2003 | Nordan et al. ............ 623/6.25 |
| 2005/0027354 A1 * | 2/2005 | Brady et al. ............... 623/6.31 |

OTHER PUBLICATIONS

Lipner, M., The near view on a new multifocal IOL, Eye-World, p. 69 (2003).

CIBA Vision, Surgical Solutions, Vivarte PRESBYOPIC—Anterior Chamber Phakic Refractive Lens, http://www.cibavision.com/products/surgical_solutions/vivarte_presbyopic.shtml (2003).

Advanced Medical Optics, Inc. (AMO), Array, Silicone Multifocal Intraocular Lens, http://www.amo-inc.com/site/products/consumers/home/asp?id=array&largeText=(2003).

Iolteck, Le Mutifocal, MG4 Implant Multificol, http://www.ioltech.com./beta/fr/zoom/zmult.htmal (2003).

Iolteck, Newlife Multifocal Implant, http://www.ioltech.com/beta/fr/zoom/newlife.html (2003).

Golub, M., et al., Diffractive Optical Elements for Biomedical Applications, SPIE, vol. 3199, pp. 220-231 (1997).

Diffractive Focuser Into Focal Line Contour, http://www.holoor.co.ll/data/ready2/products/mfr-multifocal/multil.htm (2004).

Beam Multiplication, RGP Multifocal Contact Lenses, http://www.holoor.co.ll/data/ready2/products/rgb_bi_focal/rgb_multi_focal_htm (2004).

Beam Multiplication, Soft Multifocal Contact Lenses, http://www.holoor.co.11/data/ready2/products/rgb_bi_focal/rgb_softmulti_focal.htm (2004).

Golub, M. et al., Multifocal Contact and Intraocular Lenses with Diffractive Microrelief, The 10th Meeting on Optical Engineering in Israel, Nov. 1996.

* cited by examiner

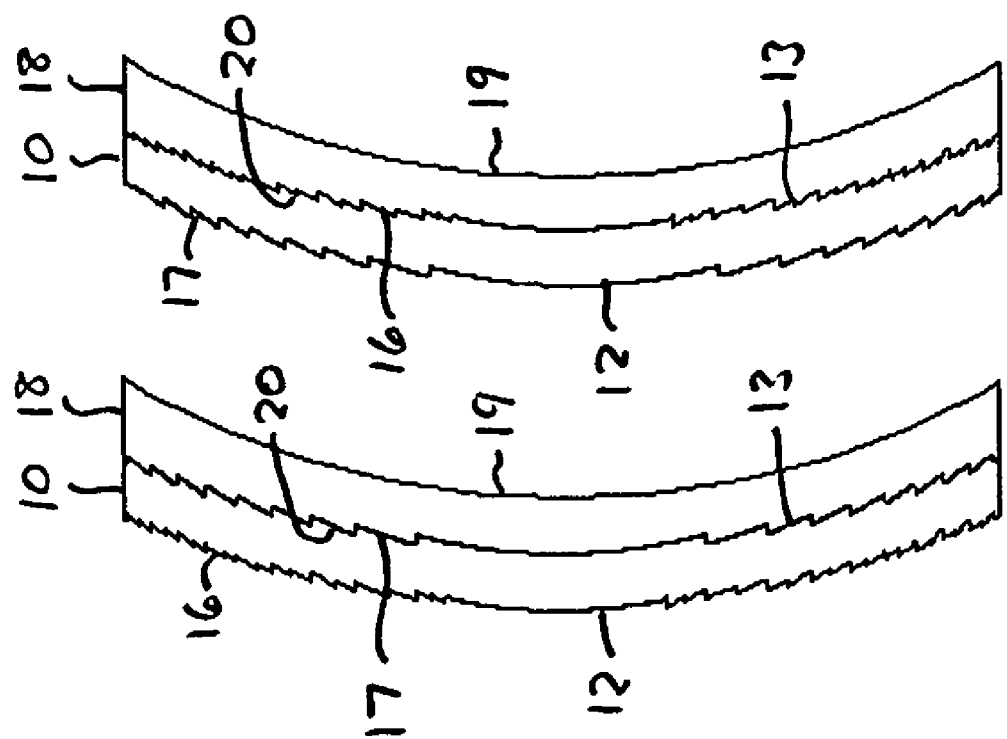

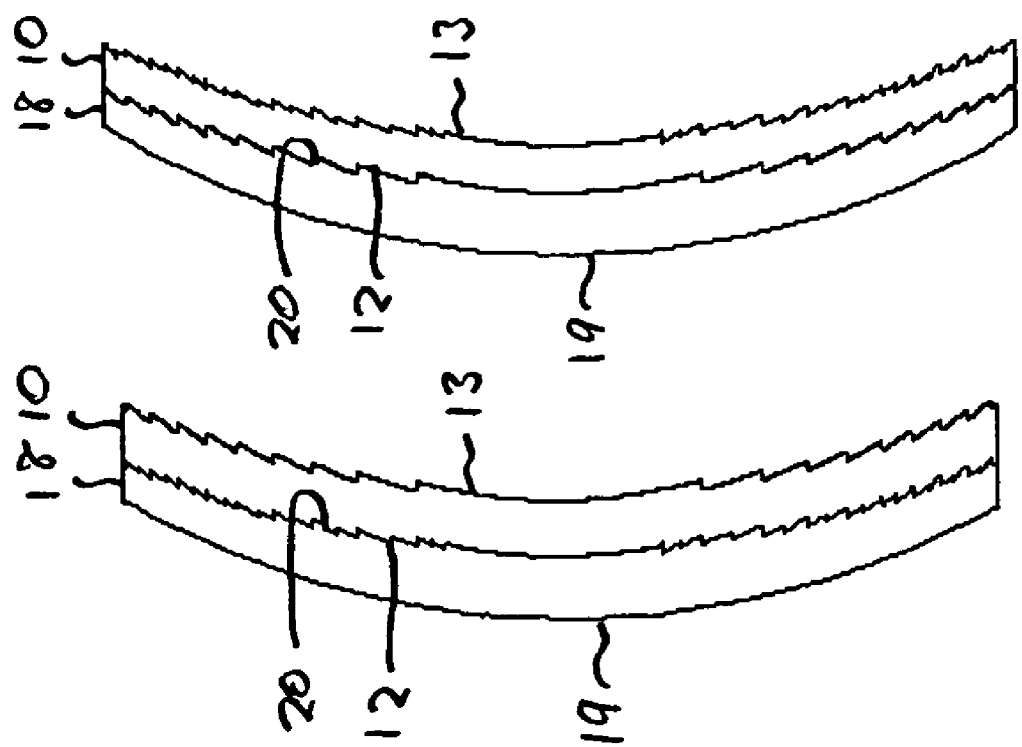

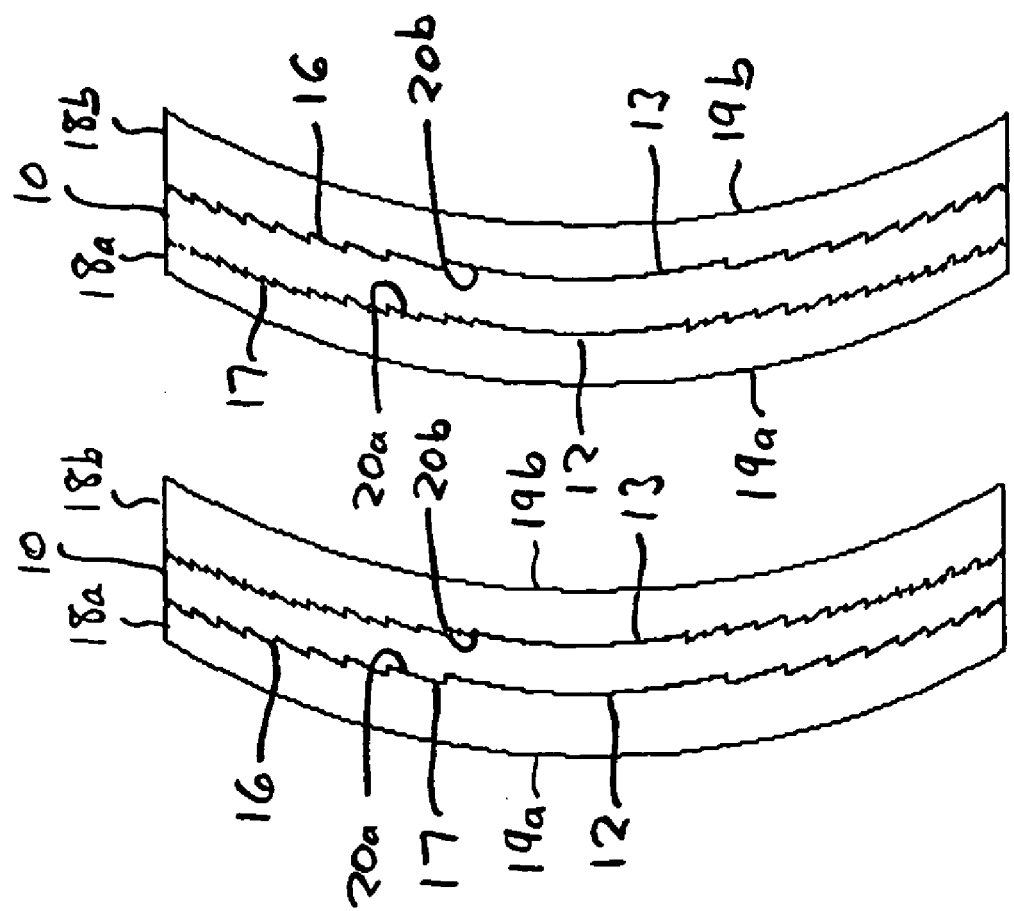

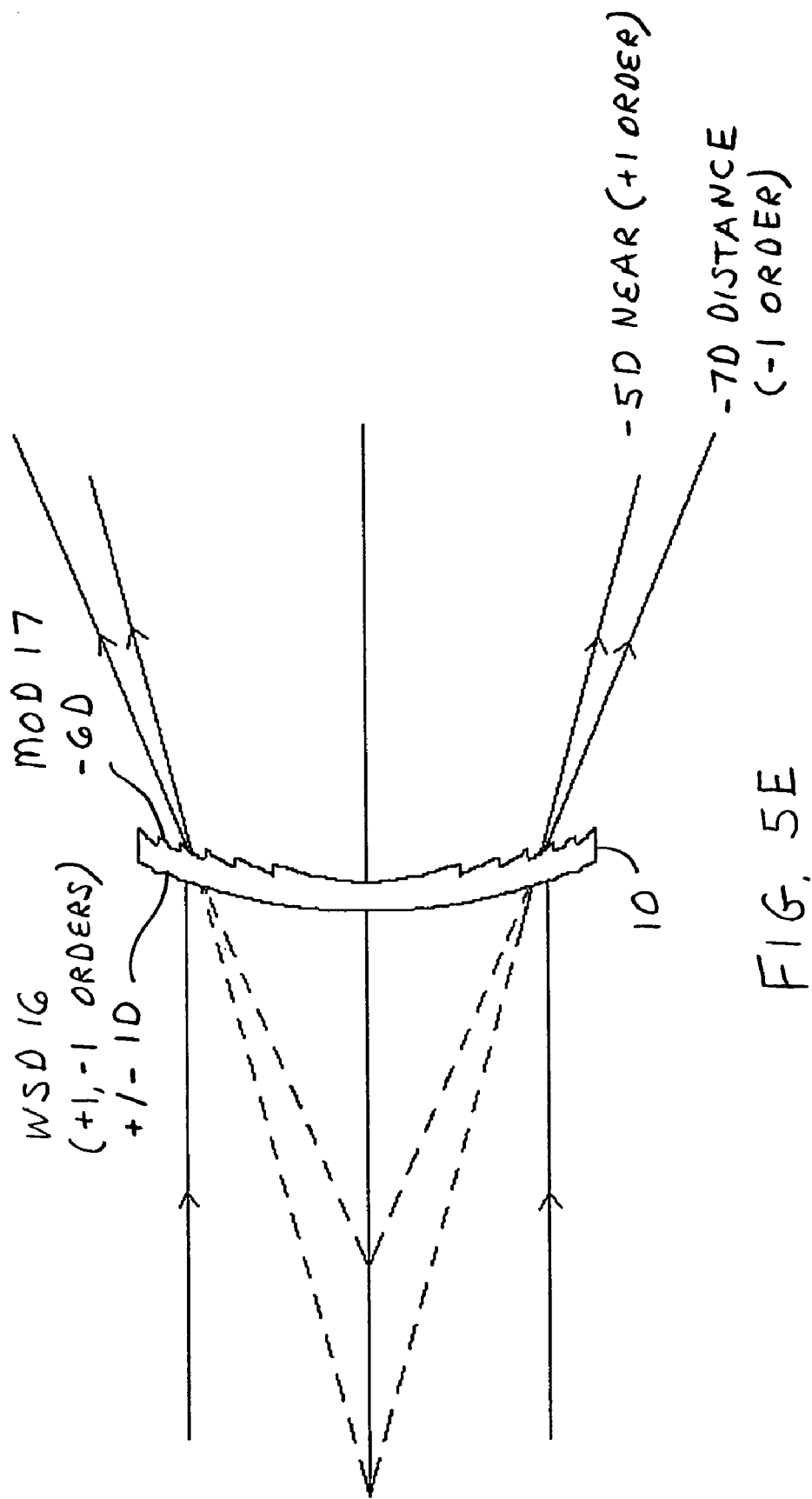

DIFFRACTIVE LENSES FOR VISION CORRECTION

FIELD OF THE INVENTION

The present invention relates to diffractive lenses for vision correction, and particularly to diffractive lenses for therapeutic vision correction at at least distance and near vision correction suitable for use with a variety of vision correction applications, such as intraocular implants (IOLs), contact lenses, or spectacle (eyeglass) lenses. The invention further relates to a method for providing such diffractive lenses.

BACKGROUND OF THE INVENTION

Multiorder diffractive (MOD) lenses are useful for bringing a plurality of spectral components of different wavelengths to a common focus, and are described in U.S. Pat. No. 5,589,982. The MOD lens has a structure of multiple annular zones having step heights defining zone boundaries, which diffract light at different wavelengths into different diffractive orders to a common focus. In contrast, viewing light of multiple different wavelengths through non-MOD diffractive multifocal lens can appear blurry since different wavelengths of light are in focus at different distances. The MOD lenses correct for this problem, but does not provide two different focal distances, e.g., near and distant, useful for providing therapeutic bifocal corrective ophthalmic lenses.

Non-MOD diffractive lenses can have a diffractive profile for diffracting different orders of light at any given wavelength to different focal distances. Such non-MOD multifocal diffractive lenses may be provided on a single lens surface or have zones divided over different surfaces of a lens. Examples of non-MOD multifocal lens are described in U.S. Pat. Nos. 5,017,000; 5,144,483; 3,004,470; 4,340,283; and 4,210,391. Still other non-MOD multifocal lenses have an additional non-MOD diffractive surface correcting for chromatic aberration, as in U.S. Pat. No. 5,117,306.

In order to provide a practical ophthalmic bifocal application utilizing non-MOD multifocal diffractive lens, refractive power can be added to the lens for distance vision correction. Hybrid refractive-diffractive lenses are described, for example, in U.S. Pat. Nos. 5,229,797; 5,104, 212; 6,120,148; 5,760,871; and 5,116,111. These hybrid refractive-diffractive lenses are thicker than non-refractive diffractive lens due to additional lens material needed to add curvature to the lens body. However, thickness reduction is often desirable in ophthalmic applications, such as contact lenses and IOLs. Thus, it would be desirable to provide a diffractive ophthalmic lens for bifocal applications which can utilize diffractive structures without the need to rely on refractive power for distance vision correction.

SUMMARY OF THE INVENTION

Accordingly, it is an object of the present invention to provide diffractive lenses utilizing a multiorder diffractive structure (MOD) and a non-MOD diffractive structure in which the combination of the two diffractive structures provides a bifocal lens having a base power for distance vision correction and an add power for near vision correction.

Another object of the present invention is to provide diffractive lenses for at least near and distance vision correction which may be adapted for use in a variety of vision correction applications, including contact lenses, intraocular implants (IOL), and spectacle lenses.

Briefly described, the present invention embodies a lens having a first diffractive structure, referred to herein as a wavefront splitting diffractive structure (WSD), for splitting light into two or more diffractive orders to different focus distances or ranges, and a second diffractive structure, referred to as a multiorder diffractive structure (MOD), for diffracting light of different wavelengths in a plurality of different diffractive orders to a common focus distance or range. The first and second diffractive structures in combination provide the lens with at least distance and near vision correction. The first and second diffractive structures may be combined on the same surface or located on different surfaces of the lens. Thus, light incident the lens is diffracted by the first diffractive structure and then by the second diffractive structure, or vice versa depending on the order of such structures in the lens, or by a single diffractive structure of the lens having a profile that combines the first and second diffractive structures.

For bifocal applications, the WSD structure has two different optical powers for each of its diffractive orders, and the MOD structure is of one optical power. The base power of the lens is provided by the combination of the optical power of the MOD structure with the optical power of the WSD structure in one of its orders, and the add power of the lens is provided by the combination of the power of the MOD structure with the power of the WSD structure in its other order.

For trifocal applications, the WSD structure has three diffractive orders to add an intermediate power when combined with the power of the MOD structure for intermediate distance vision correction between near and distance vision correction. More than three different orders may similarly be provided to the WSD structure in multifocal applications having more than three vision correction distances.

Optionally, an optical element, such as a substrate or coating, may be provided to one or both surfaces of the lens to provide the lens with smooth outer surface(s).

This MOD structure of the lens is characterized by multiple zones which define zone boundaries at which light incident on this structure experiences an optical phase shift, and diffracts light of each of the wavelengths in a different diffractive order, m, such that the magnitude of m is greater than or equal to 1, to the same focus. The zones may be radially spaced at $r_j$ and said radii are obtained by solving the equation $\phi(r_j)=2\pi p j$ where $\phi(r_j)$ represents the phase function for the wavefront emerging from the diffractive lens, and p represents the number of $2\pi$ phase jumps at the zone boundaries for one of the plurality of wavelengths where p is an integer greater than 1. The MOD structure is described in more detail in U.S. Pat. No. 5,589,982.

The present invention further provides a method for providing a bifocal ophthalmic lens by selecting a MOD structure for the lens in accordance with the needed base power of the lens, and then selecting a WSD structure for the lens, in which the base power for distance vision correction and add power for near vision correction are in accordance with a combination of the MOD and WSD structures. A trifocal or other multifocal lens may similarly be provided for one or more intermediate vision correction distances between the near and distance vision correction.

Further, refractive power optionally may be added to the lens to supplement or add to the base power already present by benefit of the MOD structure of the lens. Astigmatism may further be corrected by the lens in one or more of its diffractive structures and/or by adding refractive curvature to one or more of the surfaces with such diffractive structures.

The lenses of the present invention may be used in a variety of ophthalmic applications, such as a contact lens, a spectacle lens, or the lens of an intraocular implant (IOL), or other optics useful for vision correction of the eye.

DETAILED DESCRIPTION OF THE DRAWINGS

The foregoing objects, features and advantages of the invention will become more apparent from a reading of the following description in connection with the accompanying drawings, in which:

FIGS. 1A and 1B are plan views of the front and back surfaces, respectively, of a first embodiment multiorder diffractive lens of the present invention having a wavefront splitting diffractive (WSD) structure on the front surface and a multiorder diffractive (MOD) structure on the back surface of the lens, in which FIG. 1A shows the annular regions of the WSD structure on the front lens surface, and FIG. 1B shows the annular regions of the MOD structure on the back lens surface.

FIG. 2A is a sectional view of a lens of FIG. 1C with addition of an optical element integrated with the back surface of the lens to provide a smooth back surface;

FIG. 2B is a sectional view of a lens of FIG. 1D with addition of an optical element integrated with the back surface of the lens to provide a smooth back surface;

FIG. 3A is a sectional view of a lens of FIG. 1C with addition of an optical element integrated with the front surface of the lens to provide a smooth front surface;

FIG. 3B is a sectional view of a lens of FIG. 1D with addition of an optical element integrated with the front surface of the lens to provide a smooth front surface;

FIG. 4A is a sectional view of a lens of FIG. 1C with addition of optical elements integrated with the front and back surfaces of the lens to provide smooth front and back surfaces;

FIG. 4B is a sectional view of a lens of FIG. 1D with addition of optical elements integrated with the front and back surfaces of the lens to provide smooth front and back surfaces;

FIGS. 5A, 5B, 5C, 5D, 5E and 5F are optical ray diagrams for examples of different ones of the lens of the present invention for bifocal applications;

Figure 8:
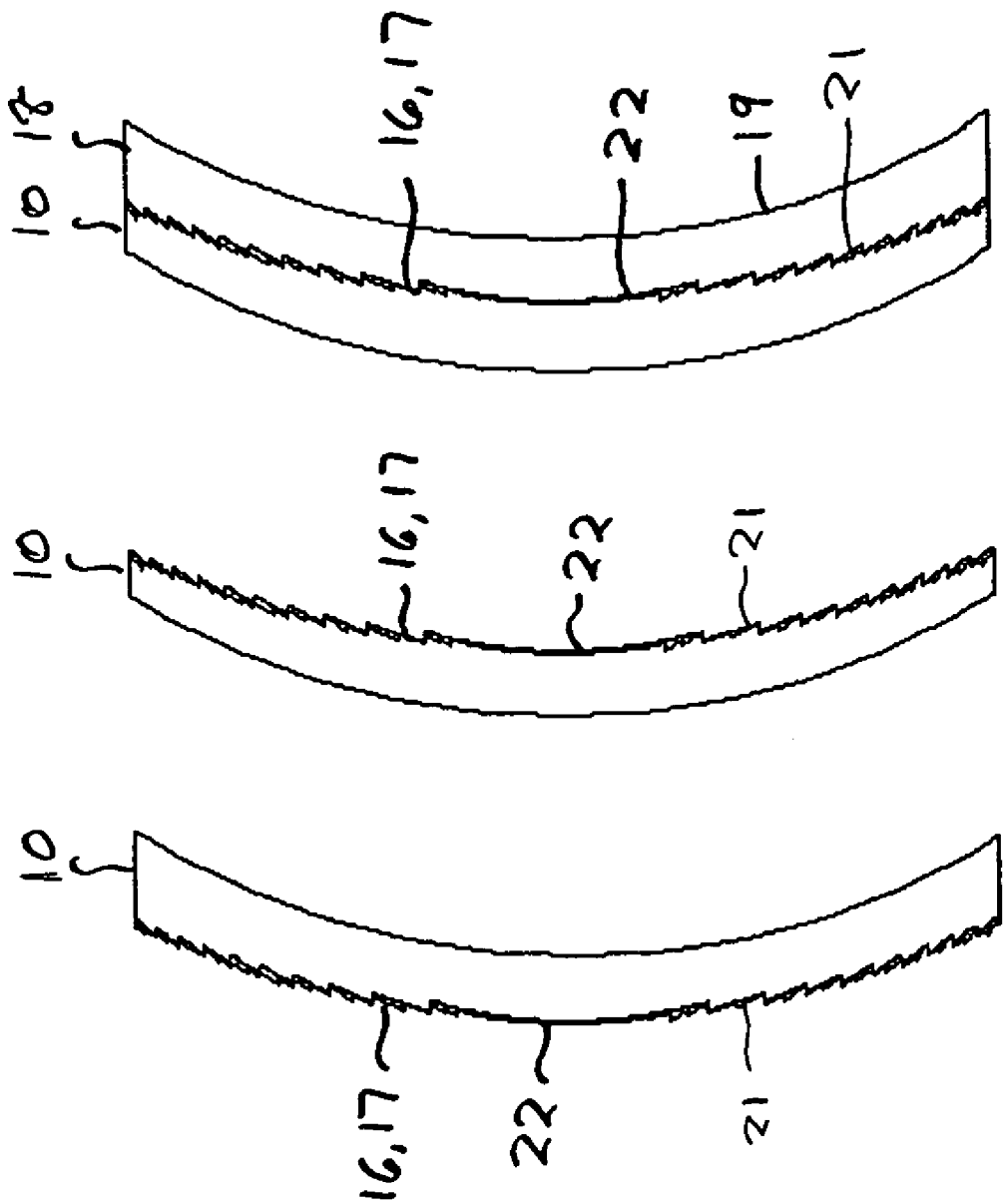
FIG. 8A is a cross sectional view of a third embodiment multiorder diffractive lens of the present invention in which the WSD and MOD structures are combined into a single profile along the front surface of the lens and the back surface has no diffractive structure.
FIG. 8B is a cross sectional view of an alternative third embodiment multiorder diffractive lens of the present invention in which the WSD and MOD structures are combined into a single profile along the back surface of the lens and the front surface has no diffractive structure.
Figure 9:
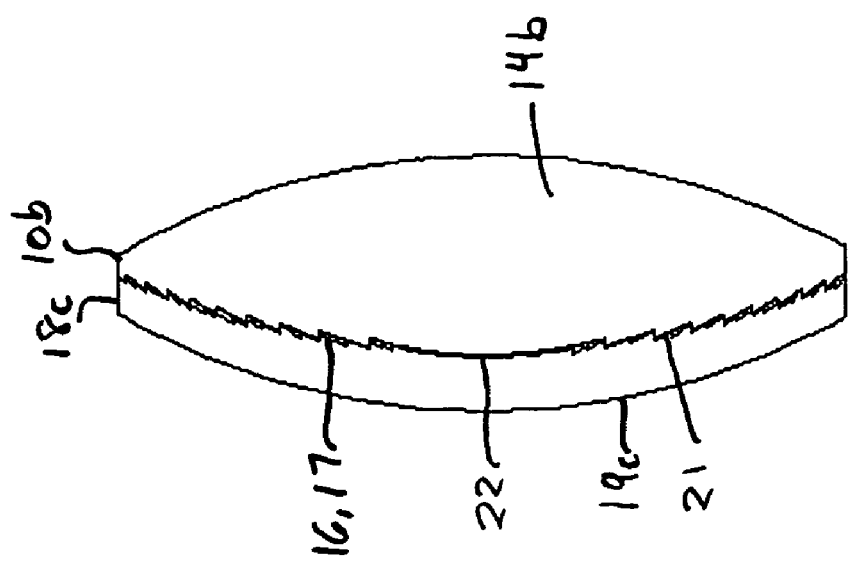

FIG. 8C is a sectional view of a lens of FIG. 8B with addition of an optical element integrated with the back surface of the lens to provide a smooth back surface; and FIG. 9 is a cross sectional view of a fourth embodiment multiorder diffractive lens of the present invention having WSD and MOD structures combined into a single diffractive structure along the back surface of the lens, where the lens body has curvature providing refractive power to the lens and an optical element is integrated with the front surface of the lens to provide a smooth front surface.

DETAILED DESCRIPTION OF THE INVENTION

Figure 1B:
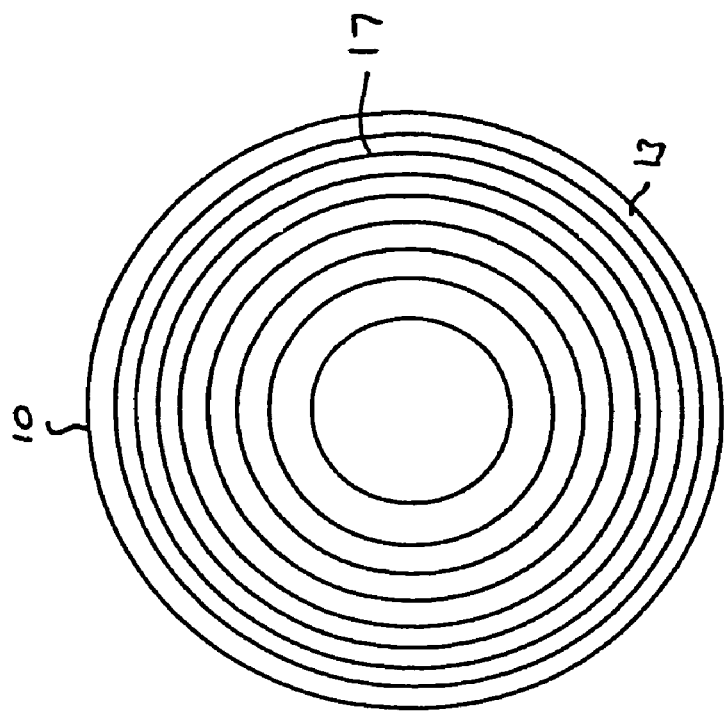
FIGS. 1A and 1B represent view of the back and front surface of this alternative lens.
Figure 1C:
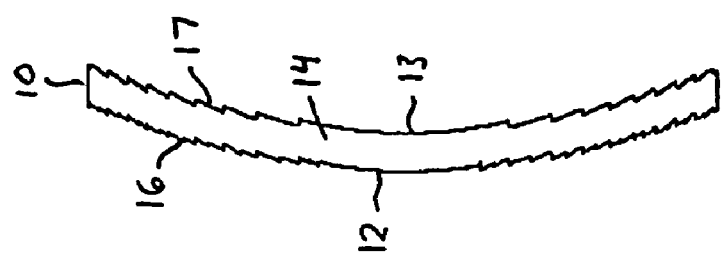
FIG. 1C is a sectional view through the lens of FIGS. 1A and 1B showing the side profile of the WSD and MOD structures on the front and back surfaces, respectively.
Figure 1A:
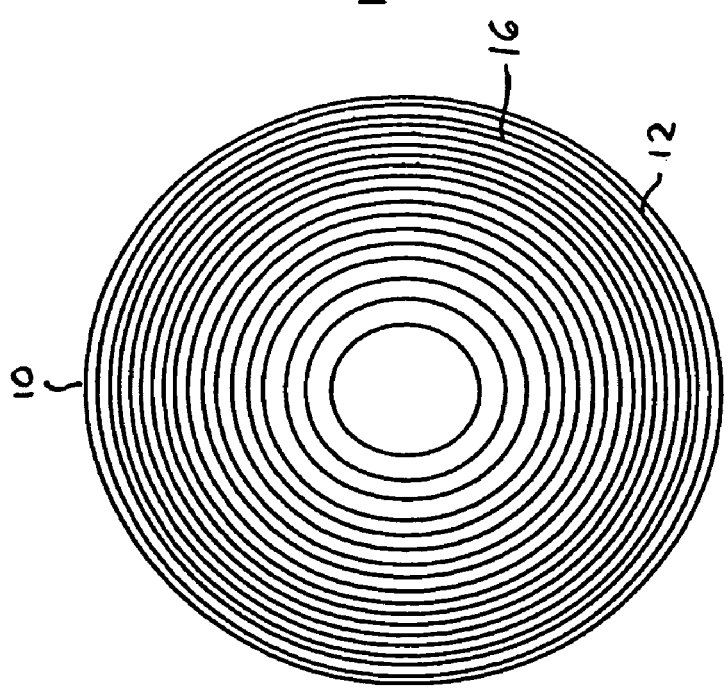
Figure 1D:
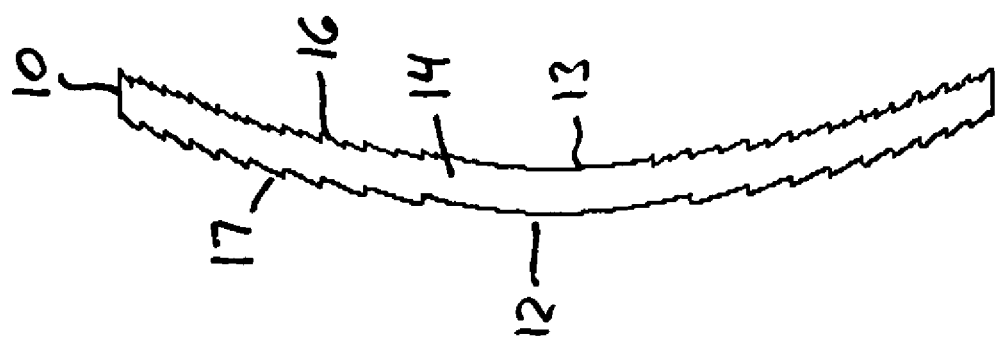
FIG. 1D is sectional view of an alternative lens of the first embodiment in which the WSD and MOD structures are profiles on the back and front surfaces, respectively, where

Referring to FIGS. 1A, 1B, and 1C, a lens 10 is shown having a front surface 12 and a back surface 13 on the sides of a single element lens body 14. The front surface 12 has a wavefront splitting diffractive (WSD) structure 16, and the back surface 13 has a multiorder diffractive (MOD) structure 17. Examples of the annular zone or regions of the WSD structure 16 and the MOD structure 17 are shown in FIGS. 1A and 1B, respectively. The curvature of the lens body 14 provides zero or near zero refractive power, and thus the lens in contact on IOL applications may be made very thin, such as, for example, 0.2–0.8 mm thick. The lens 10 diameter is in accordance with its particular ophthalmic application, contact, IOL, or spectacle. The lens in an IOL may have additional haptic or support structures as typical of IOLs, such as described, for example, in U.S. Pat. Nos. 6,406,494, 6,176,878, 5,096,285, or U.S. Patent Application Publications Nos. 2002/0120329 A1, 2002/0016630 A1, 2002/0193876 A1, 2003/0014107 A1, or 2003/0018385 A1, or without typical haptic structures, as shown in U.S. Pat. No. 4,769,033. Alternatively, the WSD structure 16 may be on the back surface 13, and the MOD structure 17 on the front surface 12, as shown in FIG. 1D.

The MOD structure 17 is described in U.S. Pat. No. 5,589,982, which is herein incorporated by reference. The MOD structure has zones with step heights providing mainly or entirely the base power for distance vision correction in accordance with the eye of the lens user.

The WSD structure 16 is a non-MOD lens which in combination with MOD structure 17 provides the add power of the lens 10 for near vision correction in accordance with the eye of the lens user. Any diffractive surface that can provide a WSD structure that has high diffraction efficiency in two or more orders (at the primary design wavelength) may be used. For example, the WSD structure may have blazed (i.e., sawtooth), sinusoidal, square wave, or other shape profile.

Lens 10 may be composed of transmissive material, such as typically used in the manufacture of contacts, optic portion of IOLs, or spectacles (e.g., plastic, silicone, glass, or polymers typically used for the particular contact, IOL, or spectacle application). Typical processes providing diffractive optical surface, such as etching, molding or direct diamond turning, may form the zones of the MOD and WSD structures on their respective surfaces of the lens. For example, single point diamond turning machinery from Precitech, Inc. of Keene, N.H. may be used to machine any diffractive structure described herein on a substrate lens material to produce the desired profile along a lens surface, or to produce a mastering tool enabling replication (e.g., by molding) of such diffractive structure in producing the lenses.

Depending on the ophthalmic application, an outer surface along the side of lens 10 with a diffractive surface may need to be smooth. Accordingly, an optical element 18 with a smooth outer surface 19 is integrated with the back surface 13 of lens 10, as shown in FIGS. 2A and 2B for lens of FIGS. 1C and 1D, respectively, or the front surface 12 of lens 10, as shown in FIGS. 3A and 3B for lens of FIGS. 1C and 1D, respectively. Optical element 18 may be a substrate or coating (applied and cured) of an optically transparent material (e.g., plastic, silicone, glass, or polymers) having an index of refraction different from the index of refraction of the lens 10 material, such that light may properly be diffracted by the diffractive structures of the lens. Optical element 18 has a surface 20 shaped with the reverse profile of the diffractive surface to face that surface when attached to lens 10. Thus when optical element 18 represents a substrate, its surface 20 mates with such diffractive structured surface when bonded thereto (e.g. liquid adhesive), fused, or otherwise sealed together.

In other ophthalmic applications, the outer surfaces of both sides of lens 10 may need to be smooth. In this case, the front surface 12 and back surface 13 of the lens of FIGS. 1C and 1D may be integrated with optical elements 18a and 18b, as shown in FIGS. 4A and 4B, respectively. Each optical element 18a and 18b has a smooth outer surface 19a and 19b, respectively, and a surface 20a and 20b, respectively, facing its respective diffractive structured surface. If needed, outer surface 19 of the optical element 18 of FIGS. 2A, 2B, 3A, or 3B, or surface 19a and 19b of optical elements 18a and 18b of FIGS. 4A and 4B, may need to be processed (e.g., cut and/or grinded) to obtain a smooth surface suitable for their ophthalmic application. Integration of optical element 18, or 18a and 18b, to provide smooth surface(s) to a diffractive surface profile may be as described, for example, in U.S. Pat. Nos. 5,129,718, 5,760,871 or 5,104,212, or in U.S. Published Application No. 2001/0018012.

The lens 10 having a MOD structure and WSD structure which combine to provide bifocal vision correction is illustrated in the following two examples.

EXAMPLE 1

In this example, an ophthalmic lens prescription requires a correction of −7 diopters (D) for distance vision, with a +2 diopters (D) add power for near vision. Thus, the two powers (denoted by $\phi$) of the lens are $\phi_{distance} = -7$ D $\phi_{near} = -5$ D$(=-7$ D$+2$ D$=\phi_{distance}+\phi_{odd})$ The lens will consist of a MOD structure 17 with the required distance power on one side (i.e., along surface 12 or 13) of a thin substrate providing the lens body 14, and with a WSD structure 16 with a blazed surface, operating primarily in the 0 and +1 orders, on the other side (or surface).

The radial locations ($r_j$) of the diffractive zones of the MOD structure are given by $$r_j = \sqrt{\frac{2jp\lambda_0}{|\phi_{distance}|}}$$

[See Equation (1) of incorporated U.S. Pat. No. 5,589,982, with $\phi_0 = 1/F_0$.]

In this example, the selected design wavelength $\lambda_0 = 555$ m (peak of photopic response). The photopic response refers to the efficiency of the human eye's perception of light wavelengths under high illumination. If p=10, the zone radii within a clear aperture diameter of 10 mm for the MOD structure are:

| MOD structure (−7 D) | |
|---|---|
| ZONE NUMBER | ZONE RADIUS |
| 0 | — |
| 1 | 1.259251 |
| 2 | 1.780851 |
| 3 | 2.181088 |
| 4 | 2.518503 |
| 5 | 2.815772 |
| 6 | 3.084524 |
| 7 | 3.331666 |
| 8 | 3.561701 |
| 9 | 3.777754 |
| 10 | 3.982103 |
| 11 | 4.176465 |
| 12 | 4.362175 |
| 13 | 4.540296 |
| 14 | 4.711688 |
| 15 | 4.877060 |

The height (h) of the zones is given by $$h = \frac{p\lambda_0}{n_{lens}(\lambda_0) - n_{medium}(\lambda_0)}$$

[See Equation (4) of the above-incorporated patent.]

where p is the MOD number of the MOD structure as discussed in above-incorporated U.S. patent, and $n_{lens}$ is the refractive index of the lens body material, and $n_{medium}$ is the refractive index of a medium, such as air or a substrate 18, 18a or 18b.

If the lens is in air, then $n_{medium}(\lambda_0)=1.0$. Also if the lens is constructed of a material with a refractive index of $n_{lens}(\lambda_0)=1.5$, this results in a height of h=11.1 µm. Alternatively, if the MOD structured surface of the lens faces a medium of refractive index $n_{medium}(\lambda_0)=1.336$, then the height of the zones increases to h=33.84 µm.

The WSD structure 16 on the other side (or surface) of the substrate providing the lens body 14 has a power equal to the add power $\phi_{odd}$. Thus, the radial locations of the diffractive zones are $$r_j = \sqrt{\frac{2j\lambda_0}{|\phi_{add}|}}$$

The zone radii within a clear aperture diameter of 10 mm are:

| Wavefront splitting structure (+2 D) | |
| --- | --- |
| ZONE NUMBER | ZONE RADIUS |
| 0 | — |
| 1 | 0.744983 |
| 2 | 1.053565 |
| 3 | 1.290349 |
| 4 | 1.489966 |
| 5 | 1.665833 |
| 6 | 1.824829 |
| 7 | 1.971040 |
| 8 | 2.107131 |
| 9 | 2.234950 |
| 10 | 2.355844 |
| 11 | 2.470830 |
| 12 | 2.580698 |
| 13 | 2.686075 |
| 14 | 2.787472 |
| 15 | 2.885308 |
| 16 | 2.979933 |
| 17 | 3.071645 |
| 18 | 3.160696 |
| 19 | 3.247307 |
| 20 | 3.331666 |
| 21 | 3.413942 |
| 22 | 3.494281 |
| 23 | 3.572814 |
| 24 | 3.649658 |
| 25 | 3.724916 |
| 26 | 3.798684 |
| 27 | 3.871046 |
| 28 | 3.942081 |
| 29 | 4.011857 |
| 30 | 4.080441 |
| 31 | 4.147891 |
| 32 | 4.214262 |
| 33 | 4.279603 |
| 34 | 4.343961 |
| 35 | 4.407380 |
| 36 | 4.469899 |
| 37 | 4.531556 |
| 38 | 4.592385 |
| 39 | 4.652419 |
| 40 | 4.711688 |
| 41 | 4.770220 |
| 42 | 4.828043 |
| 43 | 4.885182 |
| 44 | 4.941660 |
| 45 | 4.997499 |

The height of the zones for the WSD structure is selected such that a maximum of one-half of a wavelength of optical path difference (OPD) is introduced. This will result in diffraction efficiencies of 40.5% in both the 0 and +1 diffraction orders. The 0 order combines with the MOD structure to produce the distance image (since the WSD surface adds no power to the lens), while the +1 order combines with the MOD structure to produce the near image. The zone height is $$h = \frac{\lambda_0/2}{n_{lens}(\lambda_0) - n_{medium}(\lambda_0)}$$

If the lens is in air, then $n_{medium}(\lambda_0)=1.0$. Also if the lens is constructed of a material with a refractive index of $\lambda_{lens}(\lambda_0)=1.5$, this results in a height of h=0.555 μm. Alternatively, if the lens is immersed in medium of refractive index $n_{medium}(\lambda_0)=1.336$, then the height of the zones increases to h=1.69 μm.

EXAMPLE 2

This example has the same ophthalmic prescription (−7 D distance power, with a +2 D add power) as Example 1, but uses a WSD structure 16 having a square-wave diffractive surface. The square-wave surface introduces one-half wavelength of optical path difference (OPD) (or, equivalently, a phase shift of π radians) over half of each zone and zero OPD over the remaining half of the zone. Since the square-wave diffractive surface has appreciable energy in the +1 and −1 diffraction orders, the power of the MOD structure in this case is $\phi_{MOD}=-6$ D and the power of the square-wave WSD surface is $\phi_{SQw}=+1$ D. The resulting total lens powers are, as in the previous example $\phi_{distance}=\phi_{MOD}-\phi_{SQW}=-6$ D−1 D=−7 D $\phi_{near}=\phi_{MOD}+\phi_{SQW}=-6$ D+1 D=−5 D=$\phi_{distance}+\phi_{odd}$ The radial locations ($r_j$) of the diffractive zones of the MOD structure are given by $$r_j = \sqrt{\frac{2jp\lambda_0}{|\phi_{MOD}|}}$$

Again, the selected design wavelength $\lambda_0$=555 nm (peak of photopic response). If p=10, the zone radii within a clear aperture diameter of 10 mm for the MOD structure are:

| MOD lens (−6 D) | |
| --- | --- |
| ZONE NUMBER | ZONE RADIUS |
| 0 | — |
| 1 | 1.360147 |
| 2 | 1.923538 |
| 3 | 2.355844 |
| 4 | 2.720294 |
| 5 | 3.041381 |
| 6 | 3.331666 |
| 7 | 3.598611 |
| 8 | 3.847077 |
| 9 | 4.080441 |
| 10 | 4.301163 |
| 11 | 4.511097 |
| 12 | 4.711688 |
| 13 | 4.904080 |

If the lens is in air, then $n_{medium}(\lambda_0)=1.0$. Also if the lens is constructed of a material with a refractive index of $n_{lens}(\lambda_0)=1.5$, this results in a height of h=11.1 μm. Alternatively, if the MOD structured surface of the lens faces a medium of refractive index $n_{medium}(\lambda_0)=1.336$, then the height of the zones increases to h=33.84 μm.

The radial locations of the diffractive zones of the square-wave WSD structure 16 on the other side (surface) of the substrate providing the lens body 14 are:

$$r_j = \sqrt{\frac{2j\lambda_0}{|\phi_{SQW}|}}$$

The zone radii within a clear aperture diameter of 10 mm are:

| Square-wave diffractive surface (±1 D) | |
| --- | --- |
| ZONE NUMBER | ZONE RADIUS |
| 0 | — |
| 1 | 1.053565 |
| 2 | 1.489966 |
| 3 | 1.824829 |
| 4 | 2.107131 |
| 5 | 2.355844 |
| 6 | 2.580698 |
| 7 | 2.787472 |
| 8 | 2.979933 |
| 9 | 3.160696 |
| 10 | 3.331666 |
| 11 | 3.494281 |
| 12 | 3.649658 |
| 13 | 3.798684 |
| 14 | 3.942081 |
| 15 | 4.080441 |
| 16 | 4.214262 |
| 17 | 4.343961 |
| 18 | 4.469899 |
| 19 | 4.592385 |
| 20 | 4.711688 |
| 21 | 4.828043 |
| 22 | 4.941660 |

The height of the square-wave diffractive surface over half of each diffractive zone is selected such that one-half of a wavelength of optical path difference (OPD) is introduced. This results in diffraction efficiencies of 40.5% in both the +1 and −1 diffraction orders. The −1 order combines with the MOD structure to produce the distance image, while the +1 order combines with the MOD structure to produce the near image. The square-wave height is $$h = \frac{\lambda_0/2}{n_{lens}(\lambda_0) - n_{medium}(\lambda_0)}$$

If the lens is in air, then $n_{medium}(\lambda_0)=1.0$. Also if the lens is constructed of a material with a refractive index of $n_{lens}(\lambda_0)=1.5$, this results in a height of h=0.555 μm. Alternatively, if the square-wave diffractive surface of the lens faces a medium of refractive index $n_{medium}(\lambda_0)=1.336$, then the height of the square-wave increases to h=1.69 μm.

Figure 5A:
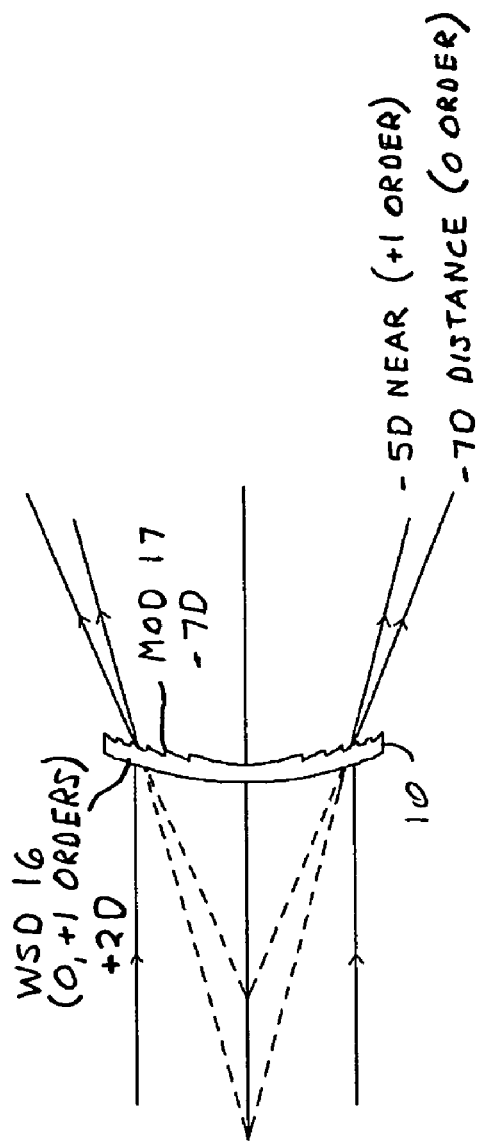
Figure 5B:
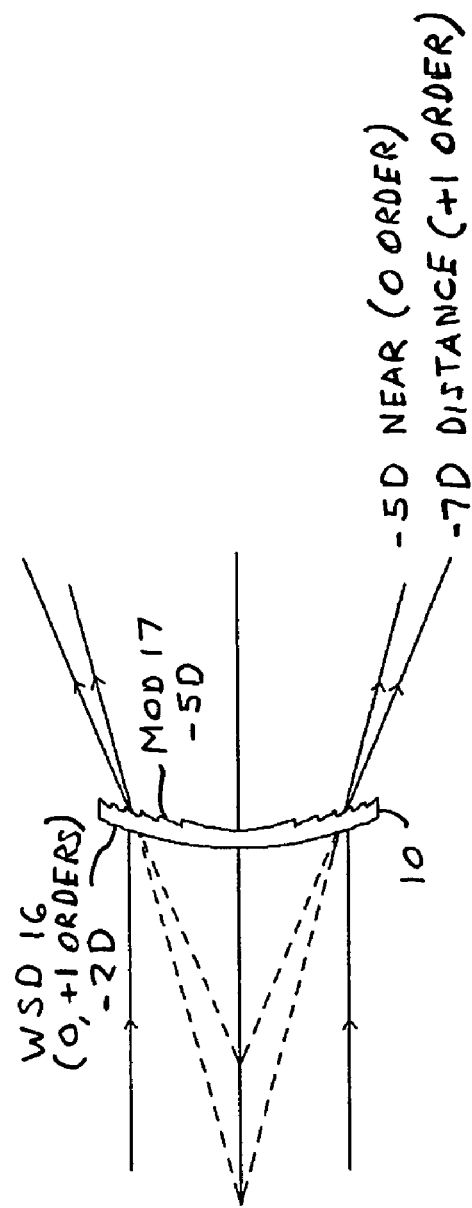
Figure 5C:
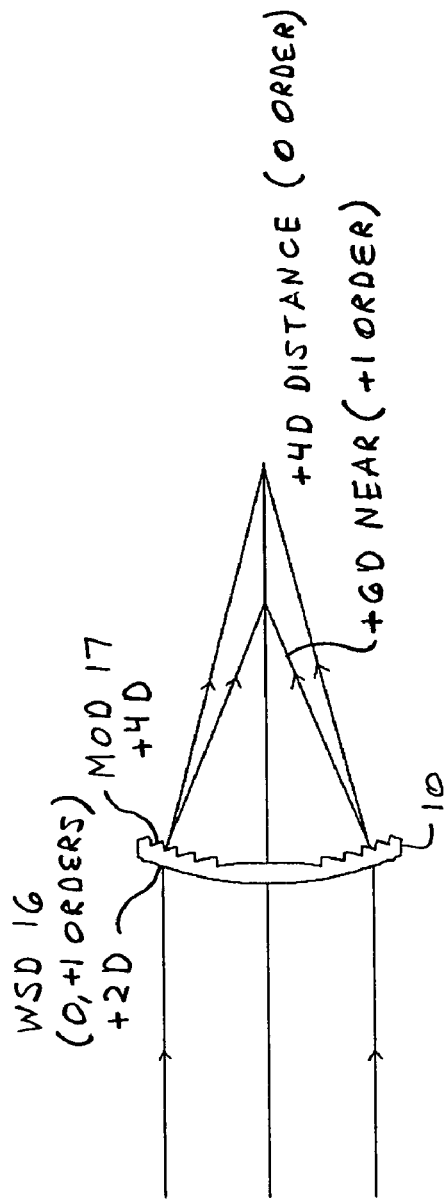
Figure 5D:
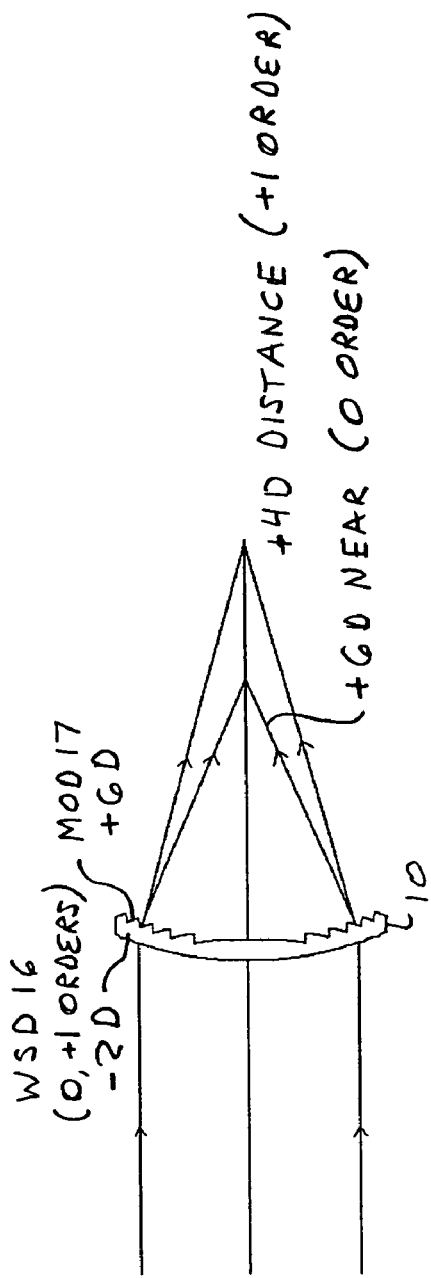
Figure 5F:
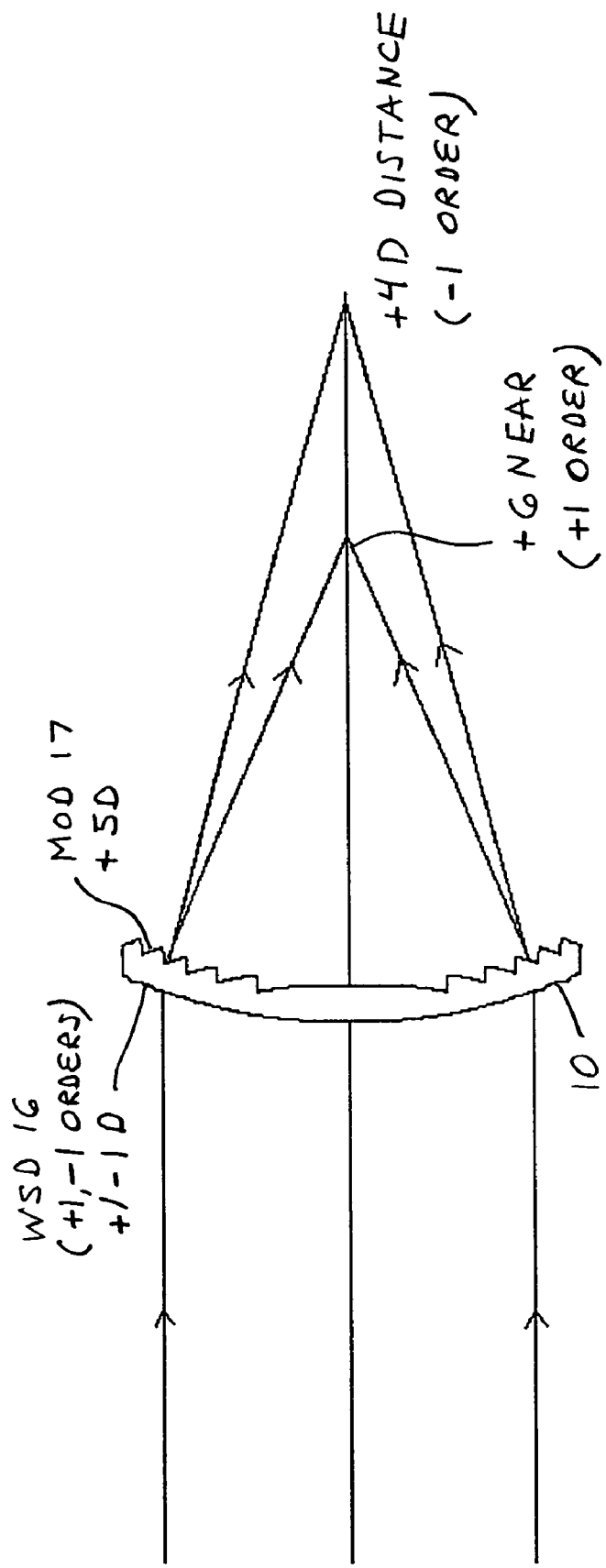

Referring to FIGS. 5A–5F, examples of optical ray diagrams for different ones of lens 10 are shown. In ophthalmic applications, the diagrams would also include the optics of the eye, such as in the case of a spectacle (i.e., lens 10 at a distance from the eye), IOL (i.e., lens 10 within the eye), or contact (i.e., lens 10 on the outer surface of the cornea). FIGS. 5A–5D show the use of different power WSD and MOD structures to provide the same bifocal prescription, but in different orders. In FIG. 5A, the lens has −5 D near (add) power in the +1 order and −7 D distance (base) power in the 0 order resulting from a +2 D power WSD structure 16 having a blazed profile (0, +1 order) and a −7 D power MOD structure 17. In FIG. 5B, the lens has a −2 D power WSD structure 16 with a blaze profile and a −5 D power MOD structure 17. In another example, the lens of FIG. 5C provides +4 D distance (base) power in the 0 order and +6 D near (add) power in the +1 order using a +2 D power WSD structure 16 and a +4 D power MOD structure 17. The lens of FIG. 5D provides a +4 D distance (base) power in the +1 order and +6 D near (add) power in the 0 order using a −2 D power WSD structure 16 and a +6 D power MOD structure 17. FIGS. 5E and 5F show a lens 10 having a WSD structure 16 with a square wave profile (+1, −1 orders) and different power MOD structures 17 of −6 D and a +5 D powers, respectively. The FIG. 5E lens results in a −5 D near (add) power in the +1 order, and −7 D distance (base) power in the −1 order. The FIG. 5F lens results in a +4 D distance (base) power in the −1 order, and a +6 D near (add) power in the +1 order. There is thus an additive effect of the power of the WSD structure in each of its diffractive orders with the power of the MOD structure to provide the bifocal near (add) and distance (base) powers. Due to the WSD structure, different wavelengths of light incident upon the lens are in focus at different distances in a range about the lens design wavelength, but since the WSD structure is much weaker in power than the MOD structure, performance is not appreciably affected. In other words, the add power and base power of a lens 10 may vary slightly at different visible wavelengths about the design wavelength due to the WSD structure.

As these examples show, different profile shapes on the WSD structured surface can be selected which when combined with a MOD structured surface, which is selected in accordance with the desired base power, provides a bifocal lens 10 with the desired near and distance vision correction. Examples 1 and 2 are illustrated for example by FIG. 5A and FIG. 5E, respectively. A sinusoidal profile could also be used, which like a square wave of FIGS. 5E and 5F, splits the light between +1 and −1 orders. In the case of a split in 0 and +1 orders, the diffractive power of the WSD structure 16 will be a full add power, while a split in +1 and −1 orders will half the add power, since this diffractive surface contributes power to both near and distant images. A diffractive surface with a +1 and −1 split has larger and fewer zones and less possible chromatic aberration, since power is less in each zone in contrast with a diffractive surface with 0 and +1 orders.

Figure 6A:
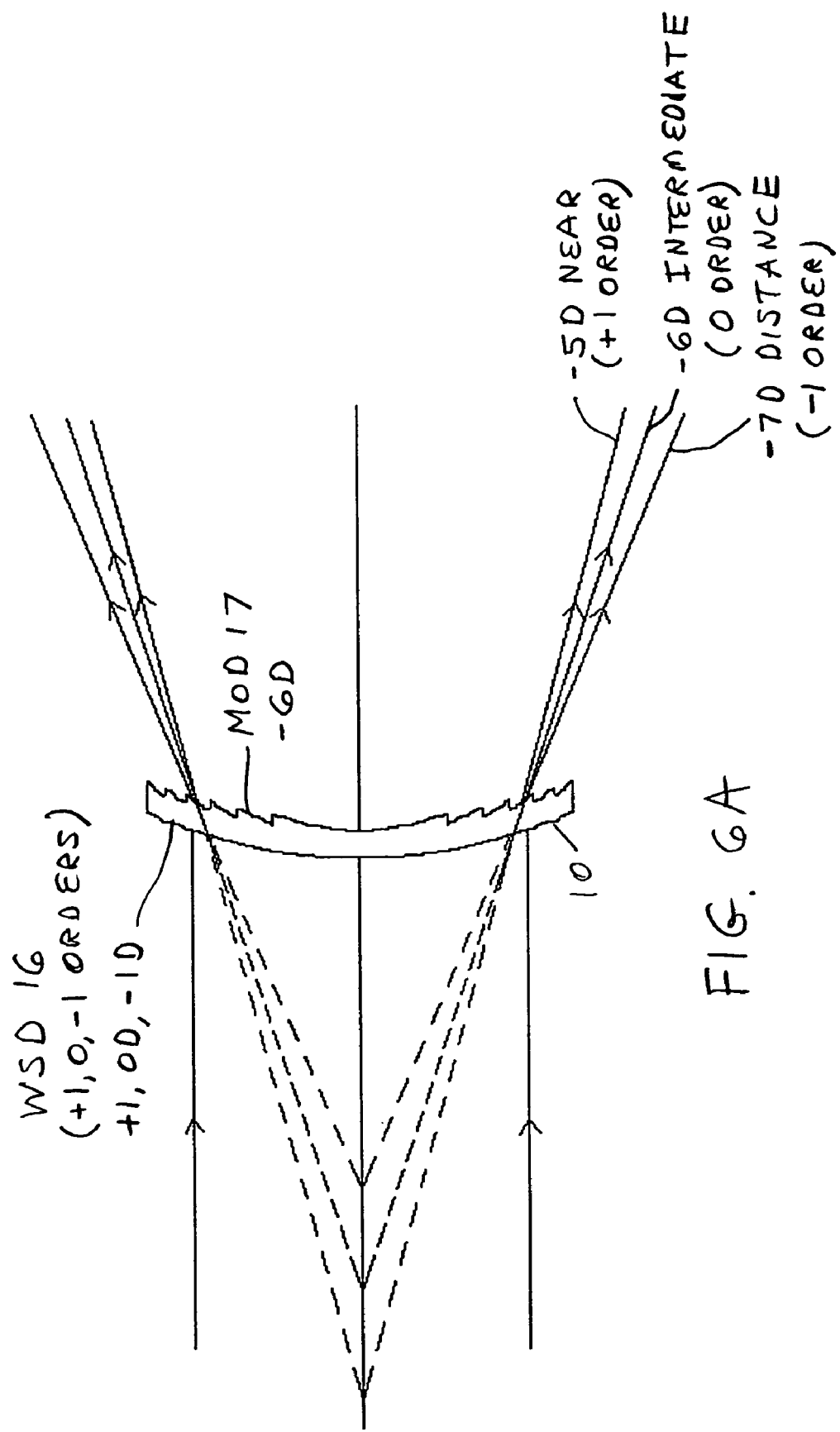
FIGS. 6A and 6B are optical ray diagrams of different ones for examples of the lens of the present invention for trifocal applications.
Figure 6B:
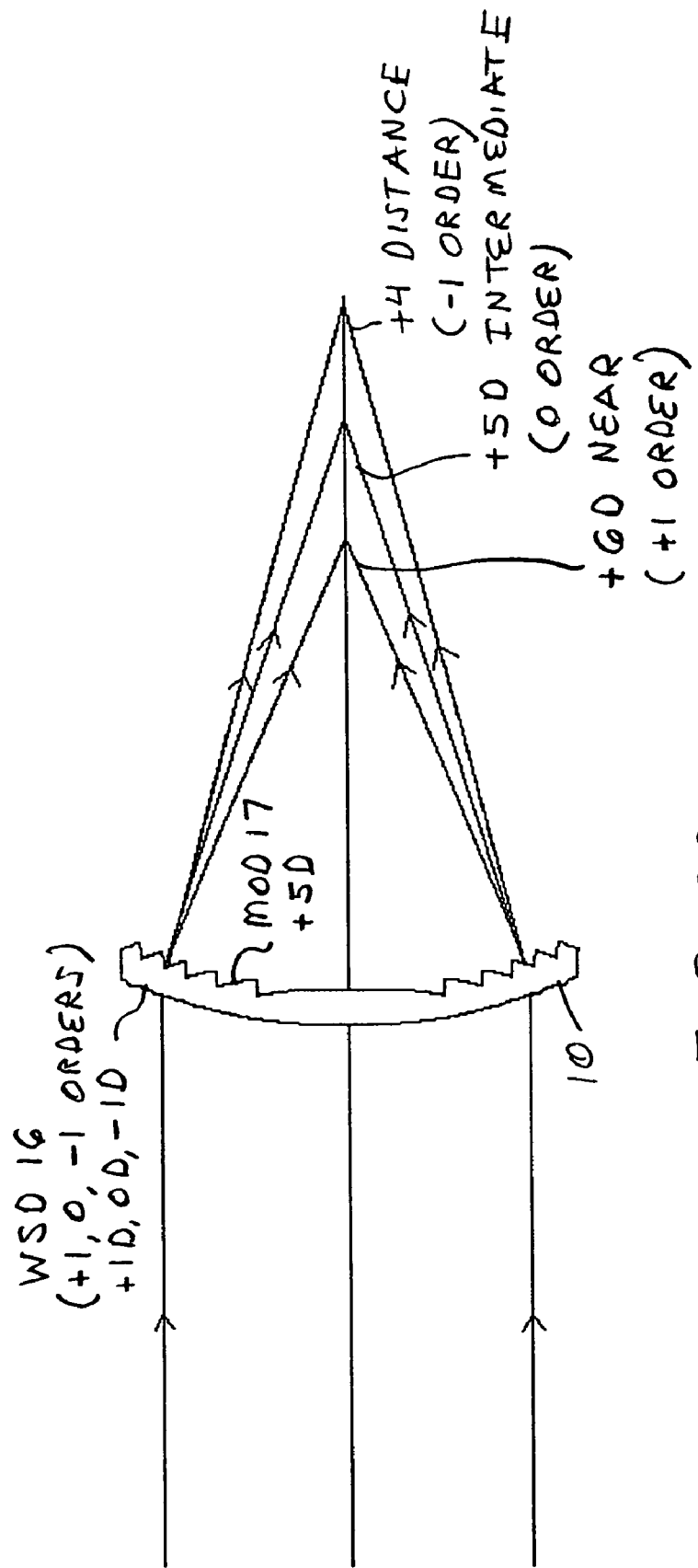

A trifocal lens may also be made with lens 10 by selecting a WSD structure 16 in which the modulation depth of a sinusoid profile is changed slightly, resulting in equal energy in the +1, 0 and −1 orders. For example, FIGS. 6A and 6B show such a WSD structure 16 with different power MOD structures of −6 D and +5 D, respectively. The FIG. 6A lens provides a −7 D distance power in the −1 order, −6 D intermediate power in the 0 order, and −5 D near power in the +1 order. The FIG. 6B lens provides +4 D distance power in the −1 order, +5 D intermediate power in the 0 order and +6 D near power in the +1 order. A WSD structure with more than three orders may be used to provide other multifocal lenses other than bifocal or trifocal.

For purposes of illustration, lens 10 of FIG. 1C is shown in FIGS. 5A–5D or 6A–6B, but any of the lens of FIGS. 1D, 2A, 2B, 3A, 3B, 4A, 4B, 5A, 5B, 7A or 7B may be used by selection of power and profile for their respective WSD and MOD structures in accordance with the examples of FIGS. 5A–5D or 6A–6B. Different powers may be used for the WSD and MOD structure of FIGS. 5A–5D or 6A–6B to provide different prescriptions as needed for the user of the lens. The number of rings shown on diffractive structures in these figures and other figures are illustrative, different number of rings, spacing, and heights may be used.

Figure 7:
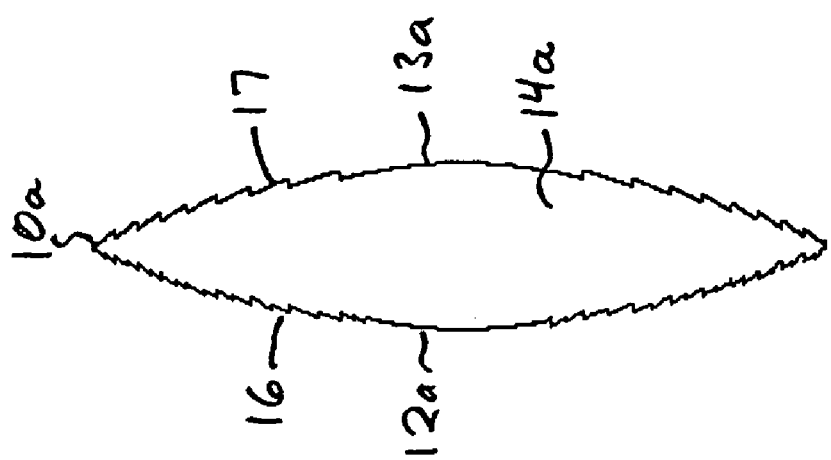
FIG. 7 is a cross sectional view of a second embodiment multiorder diffractive lens of the present invention having a first surface with WSD structure, a second surface with a MOD structure, and the lens body has curvatures providing refractive power to the lens.

Preferably, the lens 10 has little or no refractive power. Optionally, refractive power may be provided by adding curvature to lens body 14a of lens 10a, as shown in FIG. 7. Lens 10a is similar to lens 10 in that WSD structure 16 and MOD structure 17 are provided on the front surface 12a and back surface 13a, respectively. Alternatively, the WSD structure 16 and MOD structure 17 may be provided on the back surface 13a and front surface 12a, respectively. An optical element 18 may be integrated with one or both of the surfaces of the lens 10 to provide a lens or lens system with one or two smooth outer surfaces, as described earlier.

The refractive power of lens 10a combines with the MOD structure 17 and WSD structure 16 to affect the base power of the lens for distance correction. Since the MOD structure already contributes to base power of lens 10a, the amount of refractive power needed is much less than if the lens lacked the MOD structure as in prior art hybrid refractive diffractive lenses. Thus, lens 10a although thicker than lens 10, may be made much thinner by the use of the MOD structure 17 than diffractive lens with refractive power of equivalent power without a MOD structure.

Referring to FIGS. 8A–8C, the WSD structure 16 and MOD structure 17 may be combined into a single diffractive structure 21 along a surface 22 of lens 10, where FIG. 8A shows this surface 22 along the front of the lens, and FIG. 8B shows this surface on the back of the lens. An optical element 18 may be integrated with diffractive structure 21 to provide a smooth outer surface 19, as described earlier. Although preferably lens 10 of FIGS. 8A–8C has little or no refractive power, optionally curvature may be added to the lens body 14b to provide lens 10b as shown in FIG. 9. In FIG. 9, the lens 10b is illustrated with optical element 18c with smooth surface 19c in which optical element 18c is integrated with the diffractive structure 21. However, lens 10b may be provided without optical element 18c. The diffractive structure 21 represents a superposition of a WSD structure 16 superimposed on a MOD structure 17, or vice versa. Thus, for example, the same prescription of FIGS. 5A–5F and 6A–6B may be provided using a single surface 22.

Optical element 18 (FIGS. 2A, 2B, 3A, 3B, and 8C), when integrated in lens 10 becomes part of lens 10, and similarly, optical elements 18a and 18b of FIGS. 4A, 4B when integrated with lens 10 becomes part of lens 10. Also, optical element 18c of FIG. 9 becomes part of lens 10b when integrated thereto. Although lens 10, 10a and 10b are shown as a single element lens body 14, 14a, and 14b, respectively, the lens body may be a single element or composed of multiple optical elements integrated together. Further, although a single layer is illustrated for optical element 18, 18a, 18b, and 18c in the figures, the layer may be a single or multiple layers of optical elements (e.g., substrates and/or coatings).

Astigmatism may also be corrected in the lens 10, 10a, and 10b by use of non-circular zones (hyperbolic or elliptical) in one or more of the WSD structure 16, MOD structure 17, or diffractive structure 21, such as described in U.S. Pat. No. 5,016,977 for non-MOD diffractive structures. In this case, the zone spacing is different in the horizontal and vertical dimensions of the lens, rather than by the same dimension as shown in the above Examples 1 and 2. The lens may also correct astigmatism by adding refractive curvature to the profile of one or more of the surfaces with such diffractive structures. Alternatively, or in addition, astigmatism may be corrected in lens 10, 10a, and 10b by refraction in the lens body as used in typical refractive lenses.

From the foregoing description, it will be apparent that there has been provided diffractive lenses for vision correction having both MOD and WSD structures, and a method for providing such lenses. Variations and modifications in the herein described lenses in accordance with the invention will undoubtedly suggest themselves to those skilled in the art. Accordingly, the foregoing description should be taken as illustrative and not in a limiting sense.

The invention claimed is:

1. An ophthalmic lens comprising:
   a lens body having first and second surfaces;
   a first diffractive structure for splitting light of different wavelengths into two or more diffractive orders to different focal distances or ranges;
   a second diffractive structure for diffracting light into a plurality of different diffractive orders to a common focal distance or a substantially common focal distance, in which said first and second diffractive structures are located on the same or different ones of said first and second surfaces; and
   said first and second diffractive structures in combination provide at least near and distance vision correction.

2. The lens according to claim 1 wherein:
   said second diffractive structure has a second power;
   said first diffractive structure has at least two different first powers in accordance with each of said diffractive orders of said first diffractive structure;
   said lens has a base power for said distance vision correction in accordance with the combination of said second power of said second diffractive structure with one of said first powers of said first diffractive structure; and
   said lens has an add power for said near vision correction in accordance with the combination of said second power of said second diffractive structure with another one of said first powers of said first diffractive structure.

3. The lens according to claim 2 wherein said second power of said second diffractive structure mainly or entirely contributes in said combination with said first diffractive structure to said base power of said lens.

4. The lens according to claim 1 wherein said second diffractive structure represents a multiorder diffractive structure characterized by a plurality of zones which define zone boundaries at which light incident on the diffractive structure experiences an optical phase shift, and which diffract light of each of said wavelengths in a different diffractive order, m, such that the magnitude of $m \geq 1$, to the focal distance or range for the diffractive structure.

5. The lens according to claim 1 wherein said lens body has two sides providing said first and second surfaces, respectively, and said first surface is along one of said sides representing the front of said lens, and said second surface is along another one of said sides representing the back of said lens.

6. The lens according to claim 1 wherein said lens body has two sides providing said first and second surfaces, respectively, and said second surface is along one of said sides representing the front of said lens, and said first surface is along another one of said sides representing the back of said lens.

7. The lens according to claim 1 wherein said lens body has zero or near zero refractive power.

8. The lens according to claim 1 wherein said lens body provides refractive power to said lens.

9. The lens according to claim 1 further comprising an optical element, wherein one of said first surface or said second surface is integrated with said optical element, and said optical element provides said lens with a smooth outer surface.

10. The lens according to claim 1 further comprising two optical elements, wherein said first surface and said second surface are integrated with a different ones of said optical elements, and said optical elements provides said lens with smooth outer surfaces.

11. The lens according to claim 9 wherein said optical element represents one of a substrate or coating.

12. The lens according to claim 10 wherein said optical elements each represent one of a substrate or coating.

13. The lens according to claim 1 wherein said first and second diffractive structures are combined into a single diffractive structure along one of said first or second surfaces.

14. The lens according to claim 13 further comprising an optical element integrated with said lens along said one of said first and second surfaces, and said optical element provides said lens with a smooth outer surface.

15. The lens according to claim 1 wherein said lens is part of an intraocular implant.

16. The lens according to claim 1 wherein said lens represents a contact lens.

17. The lens according to claim 1 wherein said lens represents a spectacle lens.

18. The lens according to claim 1 wherein at least one of said first and second diffractive structures corrects for astigmatism.

19. The lens according to claim 1 wherein at least one of said first and second diffractive structures has refractive curvature which corrects for astigmatism.

20. The lens according to claim 1 wherein said lens body is composed of a single optical element.

21. The lens according to claim 1 wherein said lens body is composed of a plurality of optical elements integrated together.

22. The lens according to claim 1 wherein said first diffractive structure splits light energy substantially equally in each of the orders of said first diffractive structure.

23. The lens according to claim 1 wherein said first diffractive structure provides a certain amount of light into each of the orders of said first diffractive structure.

24. The lens according to claim 1 wherein said first diffractive structure has a one of a blazed, sinusoidal, or square wave profile.

25. The lens according to claim 1 wherein said lens body is sufficiently thin for use in IOL or contact lens applications.

26. The lens according to claim 1 wherein said first diffractive structure splits light into two diffractive orders, and said first and second diffractive structures in combination provide a bifocal one of said lens with near and distance vision correction.

27. The lens according to claim 1 wherein said first diffractive structure splits light into three diffractive orders, and said first and second diffractive structures in combination provide a trifocal one of said lens with near, intermediate, and distance vision correction.

28. A method for providing a bifocal ophthalmic lens having a base power and an add power comprising the steps of:
selecting a first diffractive structure for the lens for diffracting light into a plurality of different diffractive orders to a common focal distance or or a substantially common focal distance in accordance with needed base power of the lens; and selecting a second diffractive structure for the lens for splitting light into two or more diffractive orders to different focal distances or ranges in which the base power for distance vision correction and add power for near vision correction are in accordance with a combination of said first and said second diffractive structures.

29. The method according to claim 28 wherein said lens has first and second surfaces, and said first and second diffractive structures are located on the same or different ones of said first and second surfaces.

30. The method according to claim 28 wherein said first diffractive structure represents a multiorder diffractive structure characterized by a plurality of zones which define zone boundaries at which light incident on the diffractive structure experiences an optical phase shift, and which diffract light of each of said wavelengths in a different diffractive order, m, such that the magnitude of m≧1, to the focal distance or range for the diffractive structure.

31. The method according to claim 28 wherein said lens has first and second surfaces, and said method further comprises the step of:
adding to at least one surface of said lens an optical substrate providing a smooth outer surface to said lens.

32. The method according to claim 28 further comprising the step of:
selecting the body of said lens to have zero or approximately zero refractive power.

33. The method according to claim 28 further comprising the step of:
selecting the body of said lens to have refractive power.

34. The method according to claim 28 wherein at least one of said first and second diffractive structures corrects for astigmatism.

35. The method according to claim 28 wherein at least one of said first and second diffractive structures has refractive characteristics to correct for astigmatism.

36. An optical element comprising:
a lens body having first and second surfaces;
a first diffractive structure for splitting light into two or more diffractive orders to different focal distances or ranges;
a second diffractive structure for diffracting light into a plurality of different diffractive orders to a common focal distance or a substantially common focal distance, in which said first and second diffractive structures are located on the same or different ones of said first and second surfaces; and
said first diffractive structure and said second diffractive structure in combination provide a plurality of different focal distances or ranges for vision correction at different distances or ranges.

37. The optical element according to claim 36 wherein said different focal distances or ranges are two to provide a bifocal lens having near and far distance correction.

38. The optical element according to claim 36 wherein said different focal distances or ranges are three to provide a trifocal lens having near, intermediate, and far distance correction.

* * * * *